United States Patent [19]

Lowery et al.

[11] Patent Number: 5,300,023
[45] Date of Patent: Apr. 5, 1994

[54] APPARATUS AND METHOD FOR INDEPENDENT MOVEMENT OF AN INSTRUMENT WITHIN A LINEAR CATHETER

[75] Inventors: Guy R. Lowery, Mission Viejo; Steven R. Bacich, Laguna Niguel; Keith Tholin, Irvine, all of Calif.

[73] Assignee: Imagyn Medical, Inc., Laguna Niguel, Calif.

[21] Appl. No.: 84,005

[22] Filed: Jun. 29, 1993

Related U.S. Application Data

[63] Continuation of Ser. No. 780,871, Oct. 18, 1991, abandoned.

[51] Int. Cl.$^5$ .................... A61M 31/00; A61M 5/00
[52] U.S. Cl. ........................ 604/51; 604/55; 604/271
[58] Field of Search ................ 604/51-55, 604/96, 131, 158, 160, 164, 165, 161, 246, 264, 280, 271; 606/192-196

[56] References Cited

U.S. PATENT DOCUMENTS

| | | | |
|---|---|---|---|
| 4,160,446 | 7/1979 | Barrington | 604/96 X |
| 4,243,040 | 1/1981 | Beecher | 604/271 X |
| 4,321,915 | 3/1982 | Leighton et al. | 128/4 |
| 4,479,497 | 10/1984 | Fogarty et al. | |
| 4,493,711 | 1/1985 | Chin et al. | |
| 4,526,175 | 7/1985 | Chin et al. | |
| 4,604,094 | 8/1986 | Shook | 604/271 |
| 4,606,347 | 8/1986 | Fogarty | |
| 5,163,927 | 11/1992 | Woker et al. | 604/271 |

FOREIGN PATENT DOCUMENTS

| | | |
|---|---|---|
| 2406823 | 8/1975 | Fed. Rep. of Germany |
| 2823025 | 12/1979 | Fed. Rep. of Germany |
| WO8001353 | 7/1980 | PCT Int'l Appl. |
| WO9101677 | 2/1991 | PCT Int'l Appl. |

OTHER PUBLICATIONS

"A Miniature Toposcopic Catheter Suitable for Small Diameter Tortuous Blood Vessels", Goldstein et al., *Transactions of the ASME, Journal of Bio-Mechanical Engineering*, vol. 102, Aug. 1980, No. 3, pp. 221-229.
"Topo Pathfinder Catheters", *Houston Biomedical, Inc.*, TPC/15M/1087/AW.
"Everting (Toposcopic) Catheter for Broad Clinical Application", D. R. Shook et al., Transactions of the ASME, vol. 109, May 1986, pp. 168, 170, 172-174.
"The Ins and Outs of Toposcopy and The Everting catheter", D. R. Schook, *SOMA* (Jul. 1987), pp. 22-27.

*Primary Examiner*—John D. Yasko
*Assistant Examiner*—Adam J. Cermak
*Attorney, Agent, or Firm*—Gordon L. Peterson

[57] ABSTRACT

A method of positioning an elongated instrument in an everting catheter is disclosed. The everting catheter includes an inflatable everting element which circumscribes a region of the instrument and which is inflated to grip the instrument. The everting catheter and instrument extend into a patient to a desired region within the body. Flush solution is introduced between the everting element and the instrument, and the instrument is moved relative to the everting element while the flush solution is between the everting element and the instrument.

30 Claims, 2 Drawing Sheets

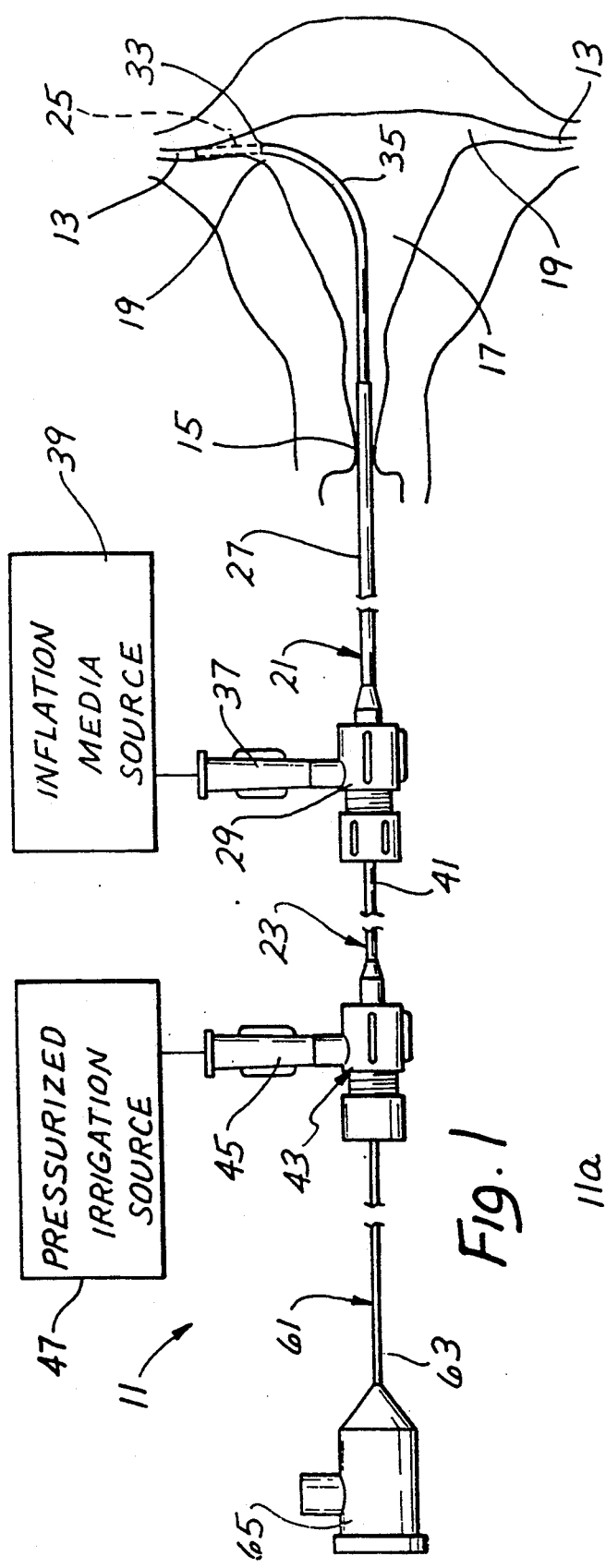
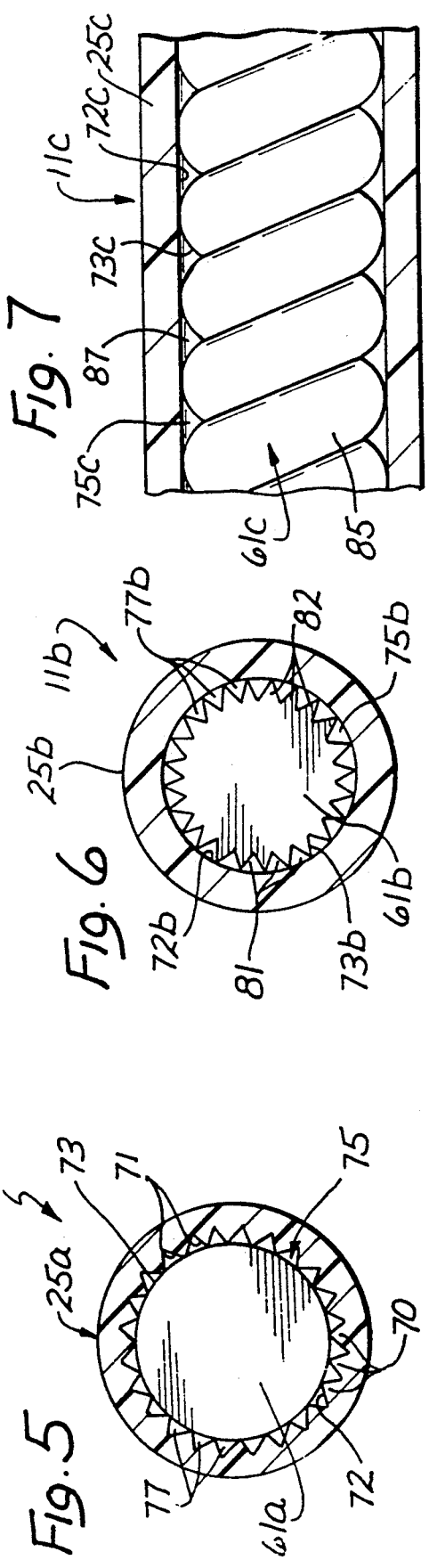

APPARATUS AND METHOD FOR INDEPENDENT MOVEMENT OF AN INSTRUMENT WITHIN A LINEAR CATHETER

This application is a continuation of application Ser. No. 07/780,871 filed Oct. 18, 1991 (now abandoned) and also entitled "APPARATUS AND METHOD FOR INDEPENDENT MOVEMENT OF AN INSTRUMENT WITHIN A LINEAR CATHETER".

BACKGROUND OF THE INVENTION

An everting catheter typically includes an outer catheter having an outer catheter lumen, an inner catheter movable longitudinally in the outer catheter lumen and having an inner catheter lumen and an everting element coupled to the outer catheter and to the inner catheter. By applying fluid pressure to the everting element and by moving the inner catheter distally in the outer catheter lumen, the everting element can be everted through the distal opening of the outer catheter. The everting element forms an extension of the inner catheter lumen.

An everting catheter is commonly used in an everting catheter system which includes an elongated instrument within the inner catheter lumen and the extension of the inner catheter lumen. With the instrument so positioned, pressurizing of the everting element causes the everting element to grip a region of the instrument.

This gripping of the instrument by the everting element is useful in that the eversion process causes the everting element to pull the instrument into the desired body region or tube. Unfortunately, this gripping action is also undesirable to the extent that the physician wishes to move the instrument independently of, and relative to, the everting element.

One prior art technique to allow for this relative movement of the instrument utilizes complete deflation of the everting element so that it no longer grips the instrument. However, deflation and subsequent reinflation of the everting element increases the time required for the procedure. Perhaps of greater importance is that deflation prevents the everting element from performing another of its functions, i.e., radially positioning of the instrument. Consequently, if the instrument is an endoscope, it is no longer radially positioned when the everting element is deflated and may actually bear against body tissue.

Another prior art solution is to employ an everting catheter of the type that never allows the everting element to grip the instrument. This can be accomplished, for example, by employing a longer inner catheter having a length that extends to the distal end of the everting element in the fully everted position or a length so great that the everting element cannot grip the balloon even in the inverted position. However, the first of these constructions also permits the everting element to grip the instrument in every position, except the fully everted position, and the second of these constructions has the disadvantage of having the inner catheter extend distally of the everting element in many positions of the everting element. If the inner catheter extends beyond the distal end of the everting element, it may damage delicate tissues.

It is also known to introduce a flush solution through an everting catheter. This may be done, for example, with a guidewire positioned in the inner catheter lumen. In this situation, the flush solution washes away blood or other material that might otherwise inhibit guidewire movement. However, the guidewire is not gripped by the everting element in that the everting element is commonly deflated prior to movement of the guidewire.

SUMMARY OF THE INVENTION

This invention provides a method and apparatus which overcomes the disadvantages noted above. With this invention, an instrument can be moved relative to the everting element of an everting catheter, and it is not necessary to evacuate the everting element or to employ everting catheters having the disadvantages noted above.

With this invention, a flush solution is introduced between the everting element and the instrument where the everting element grips the instrument. The instrument is then moved relative to the everting element while the flush solution is present between the everting element and the instrument. The flush solution lubricates the instrument-everting element interface to facilitate sliding movement, which may be rotational and/or longitudinal, of the instrument in the everting element. Preferably, the flush solution forms a layer between the everting element and the instrument and actually separates the everting element from the instrument. The instrument is then moved relative to the everting element while the everting element and the instrument are separated.

To the extent that the flush solution is between the instrument and the everting element, movement of the instrument relative to the everting element is facilitated. It is preferred, however, to have flush solution entirely around, or circumscribing, the gripped region of the instrument to make movement of the instrument relative to the everting element easier.

The concept of introducing the flush solution between the everting element and the instrument and moving the instrument relative to the everting element while the flush solution is between the everting element and the instrument is applicable whether or not there is any reduction in inflation pressure, i.e., the inflating pressure applied to the everting element. However, the introduction of flush solution and the accompanying movement of the instrument can be carried out without deflating of the everting element or without reducing the inflation pressure. Because the everting element need not be deflated or even subjected to a reduced inflation pressure during movement of the instrument, the everting element can maintain the instrument in the desired radial position within a vessel or tube while the instrument is being moved relative to the everting element.

If there is no reduction in the inflation pressure, it is necessary that the catheter system have some compliance to enable the flush solution to flow between the everting element and the instrument. This compliance can be provided by compliant system components, such as polymeric tubing and/or by employing an at least somewhat compressible inflation medium.

The pressure of the flush solution should be sufficient to flow the flush solution between the everting element and the instrument and into the patient. Generally, the pressure of the flush solution must be greater than the inflation pressure. Pressure for the flush solution may be generated by, for example, a peristaltic pump, a mechanical syringe pump, a hand-held syringe or a pressure bag of the kind typically used in hospitals. It is usually desirable that the pressure of the flush solution be only slightly greater than the inflation pressure. The pressure of the flush solution may be intermittent, pulsed or steady state.

The flush solution may be virtually any biocompatible liquid capable of separating and/or lubricating the everting element and the instrument. For example, the flush solution may be a saline solution or a contrast dye.

Although the method of this invention can be employed in different regions of the body, it is particularly adapted for use in the fallopian tubes. Thus, with the catheter and instrument in the uterus and adjacent an ostium of a fallopian tube, inflation fluid pressure is applied to the everting element to cause the everting element to grip the instrument, evert the everting element into the fallopian tube and pull the instrument along in the fallopian tube. By introducing the flush solution through the lumen of the inner catheter, the instrument can be moved in the fallopian tube longitudinally relative to the everting element while the flush solution is between the everting element and the instrument. The everting element, when everted, positions the instrument radially in the fallopian tube and preferably centers the instrument in the fallopian tube. With this invention, the flush solution can be introduced while the everting element radially positions or centers the instrument in the fallopian tube.

Although the method of this invention can be carried out utilizing a conventional everting catheter, this invention provides structural features that enhance and facilitate the method. This is accomplished, for example, by introducing the flush solution to a preformed flow passage, i.e., a flow passage that exists even when the everting element grips the instrument. This assures that the flush solution can more easily pass between the everting element and the instrument.

The preformed flow passage may be of various different configurations and may, for example, include a plurality of preformed, circumferentially spaced, generally axially extending flow paths and/or a preformed generally helically extending flow passage.

The flow passage is preferably formed by confronting surfaces on the everting element and the instrument where the everting element grips the instrument. A flow passage of any length may be useful, and so it preferably extends at least part way through the region of the instrument which is gripped by the everting element. Preferably, however, the flow passage extends entirely through such gripped region of the instrument. Specifically, the confronting surfaces of one or both of the everting element and instrument may include a plurality of grooves defining the flow passage.

In one preferred everting catheter, the inner catheter has a surface which defines the inner catheter lumen, and the everting element has a surface which defines an extension of the inner catheter lumen. At least one of these surfaces has an elongated groove defining a portion of a distally extending fluid passage which exists when the everting element is everted.

The invention, together with additional features and advantages thereof may best be understood by reference to the following description taken in connection with the accompanying illustrative drawings.

BRIEF DESCRIPTION OF THE DRAWINGS

FIG. 1 is a plan view of a catheter system which can be used to carry out the method of this invention with the catheter system accessing a fallopian tube.

FIG. 5 is an enlarged, sectional view taken generally along line 5—5 of FIG. 3 and illustrating an alternate construction for the everting element.

FIG. 6 is an enlarged sectional view on the plane of FIG. 5 illustrating an alternate construction for the instrument.

FIG. 7 is a fragmentary, axial, sectional view illustrating a second alternate construction for the instrument.

DESCRIPTION OF THE PREFERRED EMBODIMENT

Figure 2:
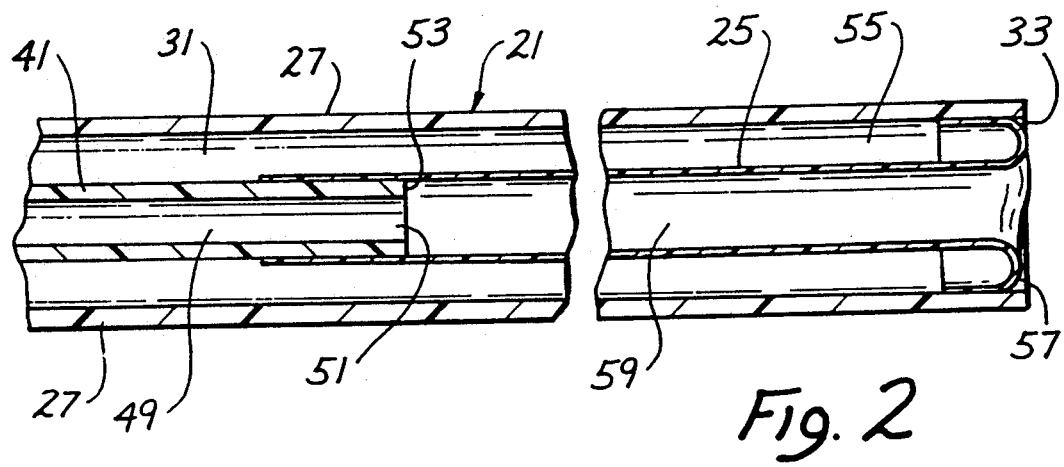
FIG. 2 is an enlarged, axial fragmentary sectional view of a distal end portion of the catheter system with the everting element in a fully inverted position. For simplicity, the distal end portion of the catheter system is shown linear rather than curved.

FIG. 1 shows a catheter system 11 which is particularly adapted for accessing fallopian tubes 13 by insertion of the catheter system through the cervix 15 into the uterus 17 of a patient to place the catheter system at an ostium 19 of one of the fallopian tubes. However, it should be understood that the features of this invention are also applicable to catheter systems adapted for other purposes.

The catheter system 11 generally comprises an outer catheter 21, an inner catheter 23 and an everting element 25 (FIG. 2). The outer catheter 21 includes an elongated, flexible catheter body 27 and an outer catheter fitting 29 coupled to the proximal end of the catheter body 27. The outer catheter 21 has an outer catheter lumen 31 (FIG. 2) which extends for the full length of the catheter body 27 and opens at a distal opening 33 (FIG. 2). Of course, the catheter body 27 may have multiple lumens, if desired, and the distal opening 33 need not be at the distal end of the catheter body.

The catheter body 27 has a distal end portion 35, which in its unstressed condition, may be straight or of any other shape designed to best gain access to a desired region of the body. As shown in FIG. 1, the distal end portion 35 is curved and forms a portion of a circular arc in the unstressed condition, and this facilitates access to the ostia 19 of the fallopian tubes 13. However, the shape of the distal end portion 35 forms no part of this invention, may be linear and is shown for convenience in FIGS. 2-4 as linear.

The outer catheter 21 may be of conventional construction, and the catheter body 27 may be constructed of a flexible, biocompatible polymeric material. The outer catheter fitting 29 has an injection leg 37 which is coupled to an inflation media source 39 for providing inflation media under pressure to the outer catheter lumen 31 to control the inversion and eversion of the everting element 25 in a known manner. The inflation media source 39 can be any known, or suitable, means for delivering inflation media under a suitable pressure to the everting element 25, such as a syringe or pump. The inflation media may be, for example, water or a contrast dye.

The inner catheter 23 is extendible through the outer catheter fitting 29 and is movable longitudinally in the outer catheter lumen 31. The inner catheter 23 also includes a catheter body 41 and an inner catheter fitting 43. The inner catheter fitting 43 has a leg 45 which is coupled to a pressurized irrigation source 47 which provides flush solution under pressure and on demand through the inner catheter fitting 43 to an inner catheter lumen 49 (FIG. 2). The inner catheter lumen 49 extends axially for the full length of the inner catheter body 41 and opens at a distal opening 51 (FIG. 2) at a distal end 53 of the inner catheter body 41. Although the pressurized irrigation source can take different forms as mentioned above, in this embodiment it is a peristaltic or syringe pump. Similarly, although there are a variety of flush solutions that can be used, in this embodiment the flush solution is water.

The catheter body 41 may be flexible or rigid depending upon the nature and purpose of the catheter system 11. However, in this embodiment, a distal region of the catheter body 41 is flexible such that the portion of the catheter body that is within the distal end portion 35 in all positions of the inner catheter 23 relative to the outer catheter 21 is flexible.

The everting element 25 is a thin, flexible membrane which is constructed of a suitable polymeric material. The everting element 25 is bonded as by a suitable adhesive to the catheter body 27 of the outer catheter 21 closely adjacent the distal opening 33 and to a distal tip region of the catheter body 41 of the inner catheter 23 in accordance with known techniques. This forms a chamber 55 with the catheter body 27 in the inverted position of FIG. 2. Consequently, inflation media from the source 39 acting in the chamber 55 can bring about inversion and eversion of the everting element 25. The everting element 25 has a distal end 57 which, in the position of FIG. 2, is substantially at the distal opening 33. The everting element 25 forms an extension 59 of the inner catheter lumen 49. In this embodiment, the outer catheter 21 and the inner catheter 23 may be of conventional construction, if desired.

Figure 3:
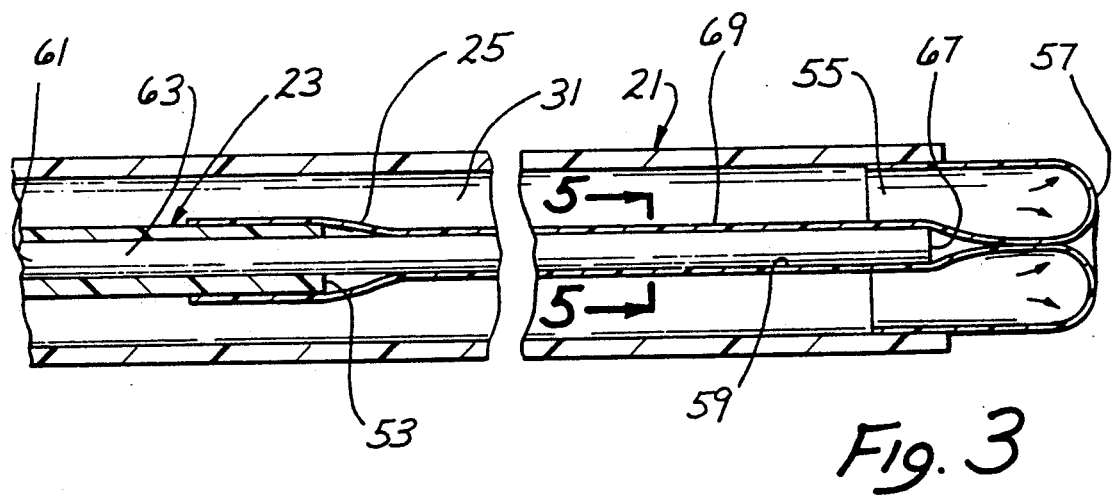
FIG. 3 is a sectional view similar to FIG. 2 with an instrument in the everting catheter and with the everting element partially everted and gripping the instrument.

The catheter system 11 also includes an instrument which, in this embodiment, is an endoscope 61. The endoscope 61 includes an elongated, flexible body 63 which extends through the inner catheter fitting 43 into the inner catheter lumen 49 and an eyepiece 65. The endoscope 61 can move both proximally and distally relative to the inner catheter 23. The endoscope 61 terminates distally in a distal end 67 as shown in FIG. 3. In this embodiment, the endoscope 61 may be conventional and may include, for example, illumination and visualization fibers which enable the physician to view an interior body region.

In carrying out the method of this invention, the catheter body 27, either with or without the endoscope 61, is located within a patient at the desired region of the body. For example for fallopian tube examination, the outer catheter 21 is inserted through the cervix 15 into the uterus 17, and the distal opening 33 is positioned in confronting relationship to an ostium 19 of a fallopian tube 13 in accordance with a known technique. This is typically accomplished with the everting element 25 in the inverted position of FIG. 2, and thereafter, the endoscope 61 is advanced through the inner catheter lumen 49 to a desired position within the extension 59.

Next, inflation media from the source 39 is introduced through the outer catheter fitting 29 and the outer catheter lumen 31 to the chamber 55. This causes the everting element to grip the endoscope 61 as shown by way of example in FIG. 3 and causes the everting element to evert into the fallopian tube 13 as shown in dashed lines in FIG. 1. Because the endoscope 61 is gripped by the everting element 25 as the everting element everts, the everting element also pulls the endoscope along into the fallopian tube 13.

It can be seen in FIG. 3 that the everting element 25 grips a region 69 of the endoscope 61. This gripping of the region 69 of the endoscope 61 by the everting element 25 prevents, or substantially prevents, moving of the endoscope 61 relative to the everting element and, in particular, it prevents relative longitudinal movement of the endoscope and the everting element.

Figure 4:
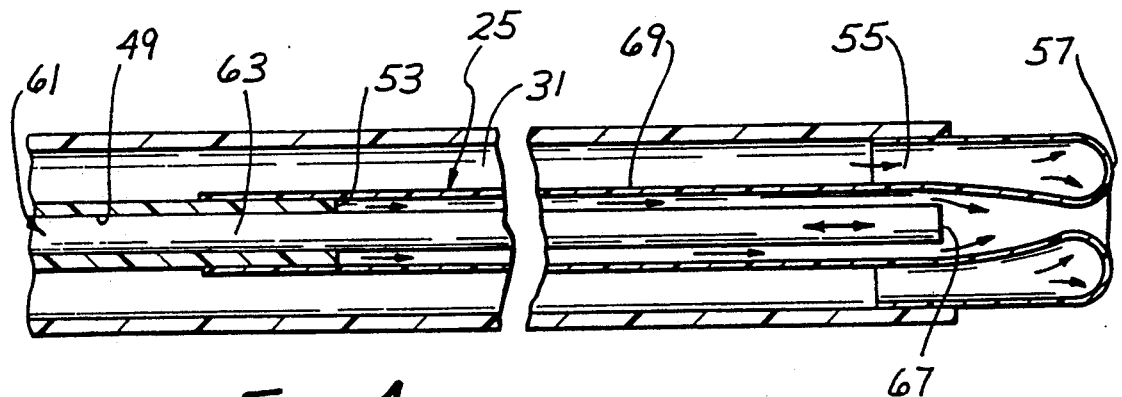
FIG. 4 is a sectional view similar to FIG. 3 with the everting element partially everted and with flush solution introduced between the everting element and the instrument to facilitate movement of the instrument relative to the everting element.

With this invention, flush solution from the irrigation source 47 is introduced through the inner catheter fitting 43 and the inner catheter lumen 49 and between the everting element 25 and the endoscope 61, where the everting element grips the endoscope, i.e., at the region 69. The flush solution lubricates the interface between the everting element 25 and the endoscope 61 at the region 69 and may form a layer of flush solution for the full length of the region 69 and completely circumferentially around the region 69. As such, this flush solution separates the everting element 25 and the endoscope 61 at the region 69. The flush solution preferably flows completely through the region 69 and exits out the distal end 57 of the everting element 25 as shown in FIG. 4. Because the flush solution between the everting element 25 and the endoscope 61 in the region 69 separates the everting element and the endoscope as shown in FIG. 4, the endoscope can be moved relative to the everting element. Such movement of the endoscope 61 may be rotational and/or longitudinal but typically is longitudinal so as to more desirably position the distal end 67 of the endoscope for viewing a desired body region, such as a region of one of the fallopian tubes 13. For example, the endoscope 61 may be moved distally from the position of FIG. 4 to place its distal end 67 at the distal end 57 of the everting element 25.

In order to obtain the flow of flush solution between the everting element 25 and the endoscope 61 at the region 69, the pressure of the flush solution from the irrigation source 47 is preferably greater than the pressure of the inflation media in the chamber 55. For example, if the inflation media is at 4 atmospheres, the pressure of the flush solution provided by the irrigation source 47 may be slightly above 4 atmospheres.

As shown, for example, in FIGS. 3 and 4, the inflated everting element 25 radially positions, and more specifically centers, the endoscope 61 in the outer catheter lumen 31 and in the fallopian tube 13 or other body vessel or tube. Preferably, the introduction of the flush solution to and through the region 69 is carried out with the everting element 25 continuing to perform its radial positioning or centering function. To best accomplish this, the steps of introducing the flush solution to and through the region 69 and the movement of the endoscope are preferably carried out without reducing the pressure of the inflation media in the chamber 55.

The catheter system 11 has sufficient compliance to allow movement of the everting element 25 off of the endoscope 61 in the region 69. Such compliance may be afforded, for example, by the everting element 25, the catheter body 27 and any tubing coupling the outer catheter fitting 29 to the inflation media source 39. When the introduction of the flush solution is terminated, the inflation media pressure within the chamber 55 again forces the everting element to grip the endoscope 61. The length of the endoscope 61 which is gripped depends upon the extent to which the everting element 25 is everted. The flush solution from the source 47 may be pulsed, intermittent or applied under steady state conditions.

It may be desirable to introduce the flush solution to a preformed flow passage between the endoscope 61 and the everting element 25. For this purpose, the embodiments of FIGS. 5–7 may be used.

FIG. 5 shows a catheter system 11a which is identical to the catheter system 11 in all respects, except for those shown or described herein. Portions of the catheter system 11a shown in FIG. 5 corresponding to portions of the catheter system 11 are designated by corresponding reference numerals followed by the letter "a."

The primary difference between the catheter systems 11 and 11a is that the everting element 25a has a plurality of axially extending splines 70 which, in this embodiment, define axially extending grooves 71 on a surface or surface region 72 at the inner catheter lumen extension 59 (FIG. 3). These grooves open radially inwardly toward the endoscope 61a and cooperate with a confronting exterior surface 73 of the endoscope to define a preformed flow passage 75 between the endoscope 61a and the everting element 25a. The flow passage 75 includes a plurality of preformed, circumferentially spaced, generally axially extending flow paths 77 between the endoscope 61a and the everting element 25a. The grooves 71 and the flow paths 77 preferably extend all of the way to the distal end 57 (FIG. 3) of the everting element. One advantage of the splines 70 and/or the grooves 71 is that they decrease surface area of contact with exterior surface 73 and reduce the friction between the surfaces 72 and 73.

The grooves 71 may be formed, as by molding them into the everting element 25a. These grooves, not only provide a flow path for the full longitudinal length of the endoscope 61a which is gripped by the everting element 25a, but because they are distributed circumferentially, assure that the flow passage 75 extends completely around the endoscope as shown in FIG. 5.

FIGS. 6 and 7 show catheter systems 11b and 11c, respectively, which are identical to the catheter system 11a in all respects not shown or described herein. Portions of the catheter systems 11b and 11c shown in FIGS. 6 and 7 corresponding to portions of the catheter system 11a are designated by corresponding reference numerals followed by the letters "b" and "c", respectively.

In the catheter system 11b, a flow passage 75b comprising a plurality of preformed, circumferentially spaced, generally axially extending flow paths 77b are provided by axially extending grooves 81 on the exterior surface 73b of the endoscope 61b. In this embodiment, the grooves 81 are defined by axially extending splines or ribs 82. Thus, the flow passages 75b, like the flow passages 75, are defined by confronting surfaces on the endoscope and the everting element. Specifically, in FIG. 6, the flow paths 77b are defined by the grooves 81 in the exterior surface 73b and a confronting surface or surface region 72b of the everting element 25b. The axial extent of the flow paths 77b and 77 may be identical, and these flow paths may also extend helically or have some other configuration, if desired.

The grooves 81 may be formed in any suitable manner on the exterior surface 73b. For example, the endoscope 61b may include a jacket having the grooves 81 formed on the external surface of the jacket.

The catheter system 11c includes an everting element 25c which is identical to the everting element 25. In the catheter system 11c, a helical flow passage 75c is defined by confronting surfaces 73c and 72c on the endoscope 61c and the everting element 25c, respectively. More specifically, the endoscope 61c has a helical rib 85 which defines a helically extending groove 87. The flow passage 75c extends axially for the same length as described above for the flow passage 75. The flow passage 75c also assures that flush solution will be provided completely around the circumference of the endoscope 61c and extend for the full length of the endoscope which is gripped by the everting element 25c.

Although exemplary embodiments of the invention have been shown and described, many changes, modifications and substitutions may be made by one having ordinary skill in the art without necessarily departing from the spirit and scope of this invention.

We claim:

1. In a method of positioning an elongated instrument in an everting catheter wherein the everting catheter includes an inflatable everting element which circumscribes a region of the instrument and which is inflated to grip the instrument and the everting catheter and instrument extend into a patient, the improvement comprising:

introducing a flush solution between the everting element and the instrument where the everting element grips the instrument; and moving the instrument relative to the everting element while the flush solution is between the everting element and the instrument.

2. An improvement as defined in claim 1 including carrying out said step of introducing without deflating the everting element.

3. An improvement as defined in claim 1 wherein there is an inflation pressure within the everting element and including carrying out said step of introducing without reducing said inflation pressure.

4. An improvement as defined in claim 1 wherein there is an inflation pressure within the everting element and wherein the step of introducing includes introducing the flush solution at a pressure greater than said inflation pressure.

5. An improvement as defined in claim 1 wherein the step of introducing includes introducing the flush solution so that it substantially circumscribes the instrument between the instrument and the everting element.

6. An improvement as defined in claim 1 wherein the everting element has a distal end and including flowing the flush solution which is introduced between the everting element and the instrument out the distal end of the everting element.

7. An improvement as defined in claim 1 wherein the step of introducing includes introducing the flush solution to a preformed flow passage between the instrument and the everting element.

8. An improvement as defined in claim 1 wherein the step of introducing includes introducing the flush solution to a plurality of preformed, circumferentially spaced, generally axially extending flow paths between the instrument and the everting element.

9. An improvement as defined in claim 1 wherein the step of introducing includes introducing the flush solution to a preformed generally helically extending flow passage between the instrument and the everting element.

10. A method as defined in claim 1 wherein the everting element and the instrument each have distal ends and the step of moving includes moving the distal end of the instrument longitudinally relative to the distal end of the everting element.

11. A method as defined in claim 10 wherein the step of moving moves the distal end of the instrument longitudinally from a first position within the everting element to a second position.

12. A method as defined in claim 10 including flowing the flush solution which is introduced between the everting element and the instrument out the distal end of the everting element.

13. A method as defined in claim 10 wherein the step of introducing includes introducing the flush solution to a preformed flow passage between the instrument and the everting element.

14. A method as defined in claim 1 wherein the everting element is everted with the everting element gripping the instrument to pull the instrument along, subsequently carrying out said step of introducing to remove the grip of the endoscope by the everting element sufficiently to permit said step of moving to be carried out.

15. In a method of positioning an elongated instrument in an everting catheter wherein the everting catheter includes an inflatable everting element which circumscribes a region of the instrument and which is inflated to grip the instrument and the everting catheter and instrument extend into a patient, the improvement comprising:
introducing a flush solution between the everting element and the instrument where the everting element grips the instrument to separate the everting element and the instrument; and
moving the instrument relative to the everting element while the everting element and instrument are separated.

16. An improvement as defined in claim 15 wherein the everting element has a distal end and including flowing the flush solution which is introduced between the everting element and the instrument out the distal end of the everting element.

17. A method of positioning an elongated instrument in an everting catheter wherein the everting catheter includes an outer catheter, an inner catheter having an inner catheter lumen and an everting element coupled to the outer and inner catheters, the instrument extends through the inner catheter lumen and the everting catheter and the instrument extend into the uterus and adjacent an ostium of a fallopian tube, said method comprising:
applying fluid pressure to the everting element to cause the everting element to grip the instrument and evert the everting element into the fallopian tube;
introducing a flush solution through the inner catheter lumen at a pressure sufficient to flow the flush solution between the everting element and the instrument when the everting element grips the instrument; and
moving the instrument in the fallopian tube longitudinally relative to the everting element while the flush solution is between the everting element and the instrument.

18. A method as defined in claim 17 wherein the everting element radially positions the instrument in the fallopian tube and said step of introducing is carried out with the everting element radially positioning the instrument in the fallopian tube.

19. A method as defined in claim 17 wherein the instrument is an endoscope, the everting element when the fluid pressure is applied generally centers the instrument in the fallopian tube and said step of introducing is carried out with the everting element centering the instrument in the fallopian tube.

20. A method as defined in claim 17 including carrying out the steps of introducing and moving without reducing the pressure of the fluid pressure applied to the everting element.

21. A method as defined in claim 17 wherein the everting element has a distal end and including flowing the flush solution which is introduced between the everting element and the instrument out the distal end of the everting element.

22. A method as defined in claim 17 wherein said step of applying causes the everting element to pull the instrument along in the fallopian tube.

23. An everting catheter system comprising:
an outer catheter having an outer catheter lumen and a distal opening leading from said outer catheter lumen;
an inner catheter movable longitudinally in the outer catheter lumen and having an inner catheter lumen;
an everting element coupled to the outer catheter and the inner catheter so that by applying fluid pressure to the everting element and with movement of the inner catheter distally in the outer catheter lumen the everting element can be everted through said opening, said everting element forming an extension of the inner catheter lumen;
an elongated instrument in the inner catheter lumen and the extension of the everting element, the pressurizing of the everting element causing the everting element to grip a region of the instrument;
said everting element and said instrument having confronting surfaces at said region of the instrument which define a helically extending flow passage when the everting element grips the instrument; and
said flow passage extending at least partly through said region of the instrument.

24. A catheter system as defined in claim 23 wherein the flow passage extends entirely through said region of the instrument.

25. An everting catheter comprising:
an outer catheter having an outer catheter lumen and a distal opening leading from said outer catheter lumen;
an inner catheter movable longitudinally in the outer catheter lumen and having an inner catheter lumen;
an everting element coupled to the outer catheter and the inner catheter so that by applying fluid pressure to the everting element and with movement of the inner catheter distally in the outer catheter lumen the everting element can be everted through said opening, said everting element forming an extension of the inner catheter lumen;
said everting element having a surface region at the extension of the inner catheter lumen; and
said surface region of the everting element when the fluid pressure is applied to the everting element having an elongated groove defining at least a portion of a distally extending fluid passage.

26. A catheter as defined in claim 25 wherein said one surface includes a plurality of elongated preformed grooves defining a plurality of flow paths.

27. A catheter as defined in claim 25 wherein the everting element has a distal end and the groove extends to said distal end.

28. An everting catheter comprising:
an outer catheter having an outer catheter lumen and a distal opening leading from said outer catheter lumen;
an inner catheter movable longitudinally in the outer catheter lumen and having an inner catheter lumen;
an everting element coupled to the outer catheter and the inner catheter so that by applying fluid pressure to the everting element and with movement of the inner catheter distally in the outer catheter lumen the everting element can be everted through said opening, said everting element forming an extension of the inner catheter lumen;
said everting element having a surface region at the extension of the inner catheter lumen; and
said surface region of the everting element having a plurality of distally extending splines.

29. An everting catheter system comprising:
an outer catheter having an outer catheter lumen and a distal opening leading from said outer catheter lumen;
an inner catheter movable longitudinally in the outer catheter lumen and having an inner catheter lumen;
an everting element coupled to the outer catheter and the inner catheter so that by applying fluid pressure to the everting element and with movement of the inner catheter distally in the outer catheter lumen the everting element can be everted through said opening, said everting element forming an extension of the inner catheter lumen;
an elongated instrument in the inner catheter lumen and the extension of the inner catheter lumen, the pressurizing of the everting element causing the everting element to grip a region of the instrument;
said everting element and said instrument having confronting surfaces at said region of the instrument which define a flow passage when the everting element grips the instrument;
the confronting surface on the everting element including a plurality of preformed grooves; and
said flow passage extending at least partly through said region of the instrument.

30. An everting catheter system comprising:
an outer catheter having an outer catheter lumen and a distal opening leading from said outer catheter lumen;
an inner catheter movable longitudinally in the outer catheter lumen and having an inner catheter lumen;
an everting element coupled to the outer catheter and the inner catheter so that by applying fluid pressure to the everting element and with movement of the inner catheter distally in the outer catheter lumen the everting element can be everted through said opening, said everting element forming an extension of the inner catheter lumen;
an elongated instrument in the inner catheter lumen and the extension of the inner catheter lumen, the pressurizing of the everting element causing the everting element to grip a region of the instrument;
said everting element and said instrument having confronting surfaces at said region of the instrument which define a flow passage when the everting element grips the instrument;
said flow passage extending at least partly through said region of the instrument; and
one of the confronting surfaces having splines to reduce friction between the confronting surfaces.

* * * * *